US012122037B1

(12) United States Patent
Williams

(10) Patent No.: US 12,122,037 B1
(45) Date of Patent: Oct. 22, 2024

(54) GRIPPING ASSISTANCE TOOL

(71) Applicant: The Real Help-Mate Inc., Philadelphia, PA (US)

(72) Inventor: Edward Williams, Philadelphia, PA (US)

(*) Notice: Subject to any disclaimer, the term of this patent is extended or adjusted under 35 U.S.C. 154(b) by 601 days.

(21) Appl. No.: 17/503,411

(22) Filed: Oct. 18, 2021

Related U.S. Application Data

(60) Provisional application No. 63/094,446, filed on Oct. 21, 2020.

(51) Int. Cl.
| | | |
|---|---|---|
| B25J 1/02 | (2006.01) |
| A61F 4/00 | (2006.01) |
| B25J 15/00 | (2006.01) |
| B25J 18/02 | (2006.01) |
| B25J 18/04 | (2006.01) |

(52) U.S. Cl.
CPC ............... *B25J 1/02* (2013.01); *A61F 4/00* (2013.01); *B25J 15/0028* (2013.01); *B25J 18/025* (2013.01); *B25J 18/04* (2013.01)

(58) Field of Classification Search
CPC ........ B25J 1/02; B25J 15/0028; B25J 18/025; B25J 18/04; A61F 4/00
See application file for complete search history.

(56) References Cited

U.S. PATENT DOCUMENTS

| | | | | |
|---|---|---|---|---|
| 5,647,622 A | * | 7/1997 | Schectman | ............... B25J 1/02 294/111 |
| 7,862,524 B2 | * | 1/2011 | Carignan | ............... B25J 17/025 601/5 |
| 9,610,684 B1 | * | 4/2017 | Easterling | .................. B25J 1/02 |
| 9,827,678 B1 | * | 11/2017 | Gilbertson | .......... A47L 11/4055 |
| 2012/0237319 A1 | * | 9/2012 | Jacobsen | ................. B25J 5/005 414/1 |
| 2018/0281207 A1 | * | 10/2018 | Tanaka | ................ B25J 15/0052 |

* cited by examiner

*Primary Examiner* — Stephen A Vu
(74) *Attorney, Agent, or Firm* — Gugliotta & Gugliotta, LPA

(57) ABSTRACT

A reaching and grabbing assist device is provided having a reaching extension for aid in reaching out of distance objects. The distal terminus of the extension has an articulating grapnel that may be angularly positioned about the lateral centerline of the shaft. A support strip on the user's wrist allows total control without the risk of the device falling out of one's grasp or reach. Made of a hard outer casing, the shaft may allow internal rigging to connect the articulating grapnel to controls at the handle. The instant abstract is neither intended to define the invention disclosed in this specification nor intended to limit the scope of the invention in any way.

8 Claims, 4 Drawing Sheets

GRIPPING ASSISTANCE TOOL

RELATED APPLICATIONS

The present invention claims benefit of U.S. Provisional Application 63/094,466, filed on 21 Oct. 2020 and incorporated by reference as if fully rewritten herein.

BACKGROUND OF THE INVENTION

1. Field of the Invention

The present invention relates generally to reach extension tools and, more particularly, to a multi axial reaching and grasping assistance device.

2. Description of the Related Art

Many people live life with the challenges of a physical disability, sometimes for a certain period and some times for their entire lives. In the United States, about 26 million people and worldwide about 130 million people that have some form of severe disability. In the U.S., 1.6 million people are using wheelchairs and 7.4 million people are using some other form of technology assistance device. Even with improvements in pre-natal healthcare that can identify and minimize the effects of congenital or childhood acquired types of disabilities, with a growing, aging population, such a community will continue to exist, between accidents, injuries and illnesses.

While many different causes of disability can exist, many have common impact that can often affect basic activities of daily living, such as eating, dressing, transferring, and maintaining personal hygiene; or advanced activities of daily living such as shopping, food preparation, driving, or working.

Currently available as mobility aids are "grabber reacher tools" as exemplified generically in FIG. 1A. Such as tool 10 provides and extension arm 12, that is foldable or non-foldable, with a grasping distal end 14 operated by a manual trigger 16a and handle 16b at a proximal end 17. As shown in conjunction with FIG. 1B, such a tool 10 includes a grabber claw 18 at the distal end where a user can access an object 20 that would otherwise be outside the user's reach.

While such devices are readily available and simple to use, they still generally require a user to have full function and mobility of at least one arm and hand in order to be of any benefit. For those unable to grip the handle 16b adequately, or have enough hand strength to operate the trigger 16a, such a device fails to provide functional assistance.

Consequently, a need exists for a reaching, grasping tool that can be easily operated even by those having more severe physical impairments.

SUMMARY OF THE INVENTION

It is thus an object of the present invention to provide an improved grasping tool for aiding users to acquire objects at a distance from their unaided reach.

It is a feature of the present invention to provide a reaching tool that allows for grasping objects at a distal end that is operated by motorized mechanism operated at a proximal end.

Briefly described according to a preferred embodiment of the present invention, a reaching and grabbing assist device is provided having a reaching extension for aid in reaching out of distance objects. While it can be used by anyone, especially while shopping where merchandise may be stored on high shelving, such an extension may be particularly useful to those disabled in wheel chairs, the little people community or those that are bedridden. The distal terminus of the extension has an articulating grapnel that may be angularly positioned about the lateral centerline of the shaft. A support strip on the user's wrist allows total control without the risk of the device falling out of one's grasp or reach. Made of a hard outer casing, the shaft may allow internal rigging to connect the articulating grapnel to controls at the handle.

While the present invention may be used by anyone in the general public, it is particularly well suited to aid those who are wheelchair mobile or bedridden.

Further, the present invention can aid in use throughout the home or in the marketplace to provide those having physical disabilities with greater autonomy and a higher quality of life.

Further still, the present invention is capable of being insurance reimbursable in the right circumstances when prescribed by a healthcare provider.

Further objects, features, elements and advantages of the invention will become apparent in the course of the following description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the Figures. It should be understood that the legal scope of the description is defined by the words of the claims set forth at the end of this patent and that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

For purposes of the present disclosure the terms "a" and "an" herein do not denote a limitation of quantity, but rather denote the presence of at least one (1) of the referenced items. Further for purposes of the present disclosure the terms "in", "out", "left" "right", "up" or "down" are all spacial and functionally relative directions used to aid in the description to best explain the principles of the invention and its practical application, and to aid others skilled in the art to best utilize the invention and are not meant to be limiting to any particular orientation. It should also be understood that, unless a term is expressly defined in this patent there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. § 112 (f).

Figures 1A, 1B:
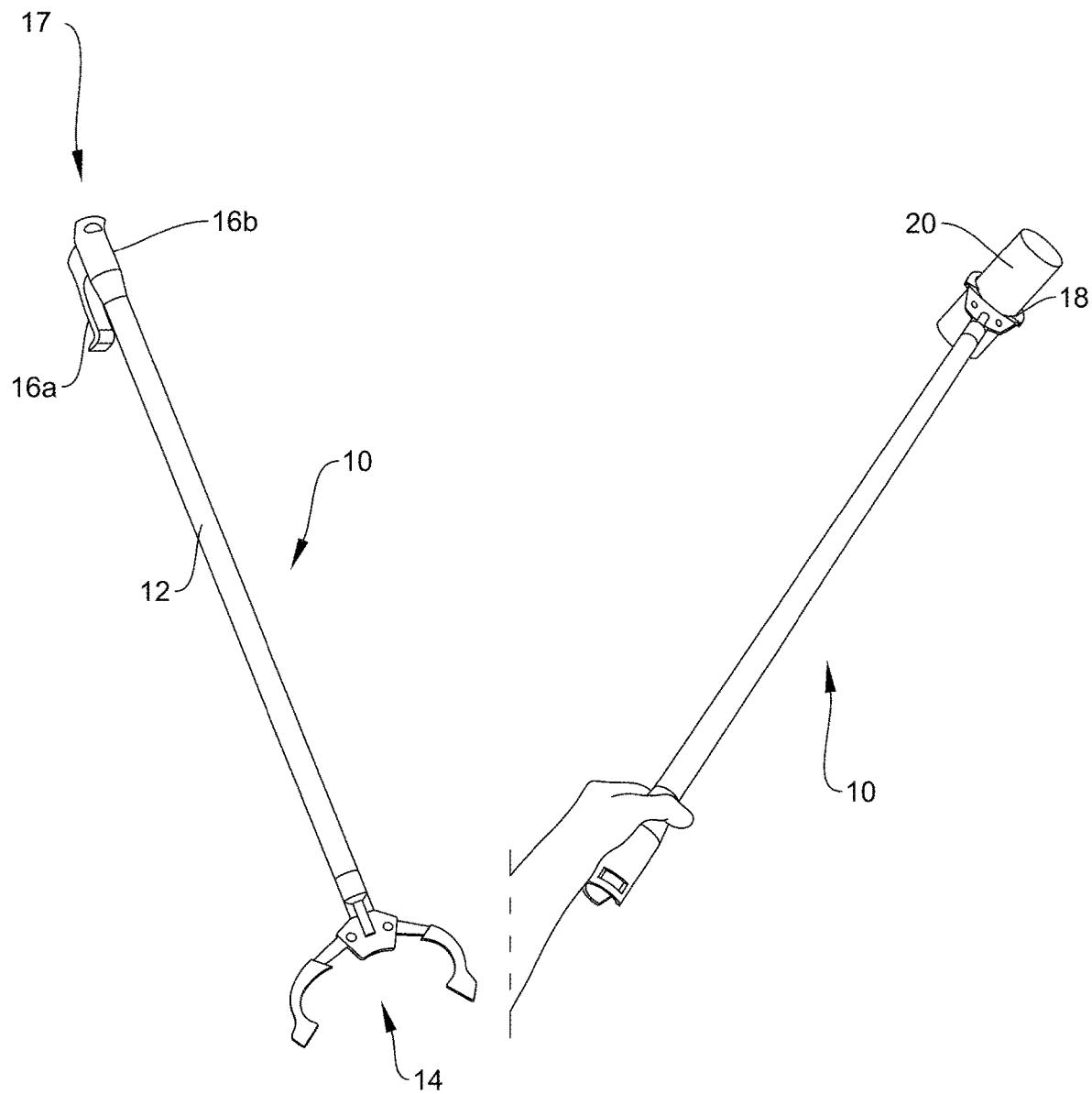
FIG. 1A is a perspective schematic of an exemplary grabber reacher tool according to the PRIOR ART.
FIG. 1B is an illustrative schematic of the grabber reacher tool of FIG. 1A shown in an exemplary use.
Figure 2:
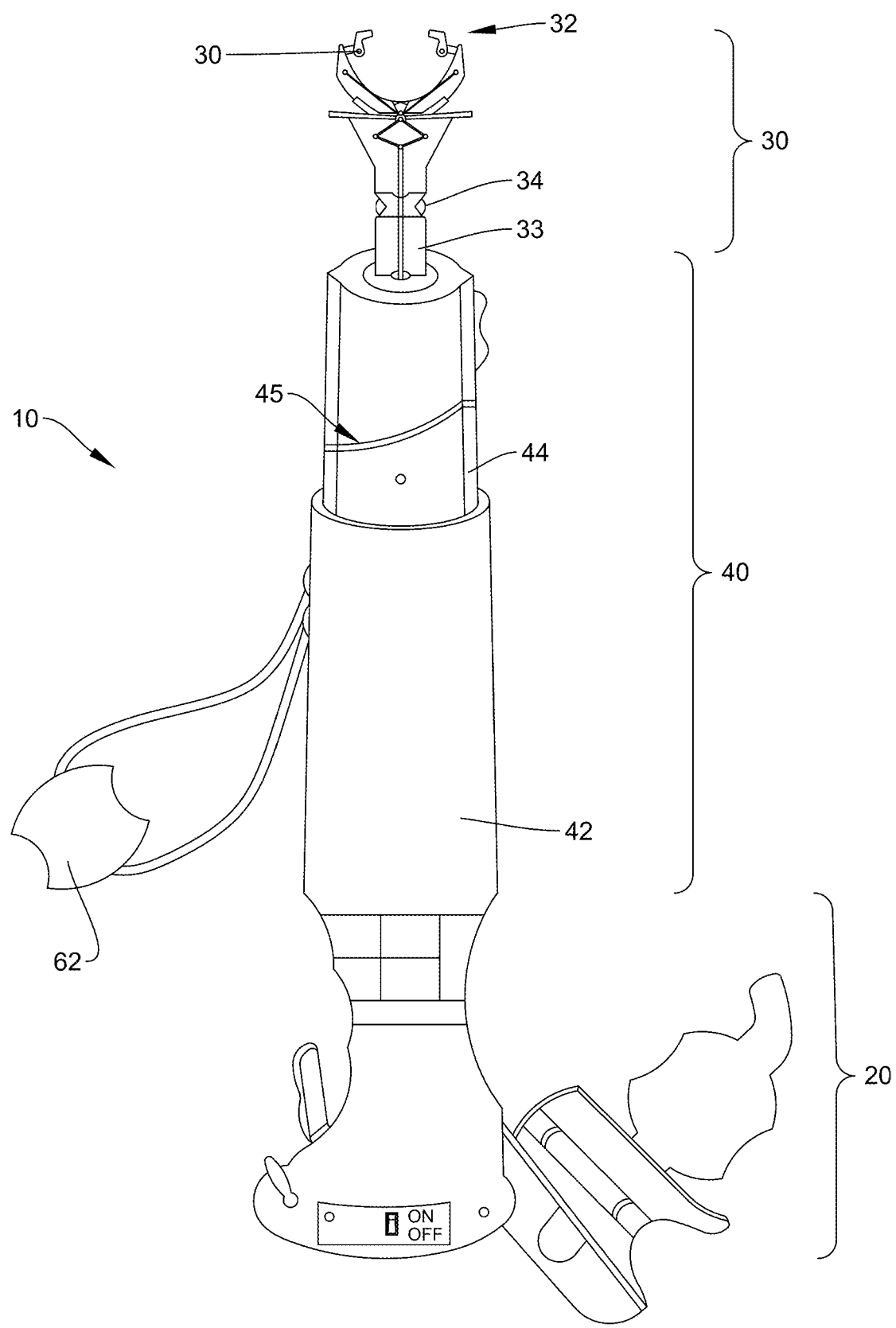
FIG. 2 is a perspective view of a reaching and grabbing assist device according to a preferred embodiment of the present invention.
Figure 3:
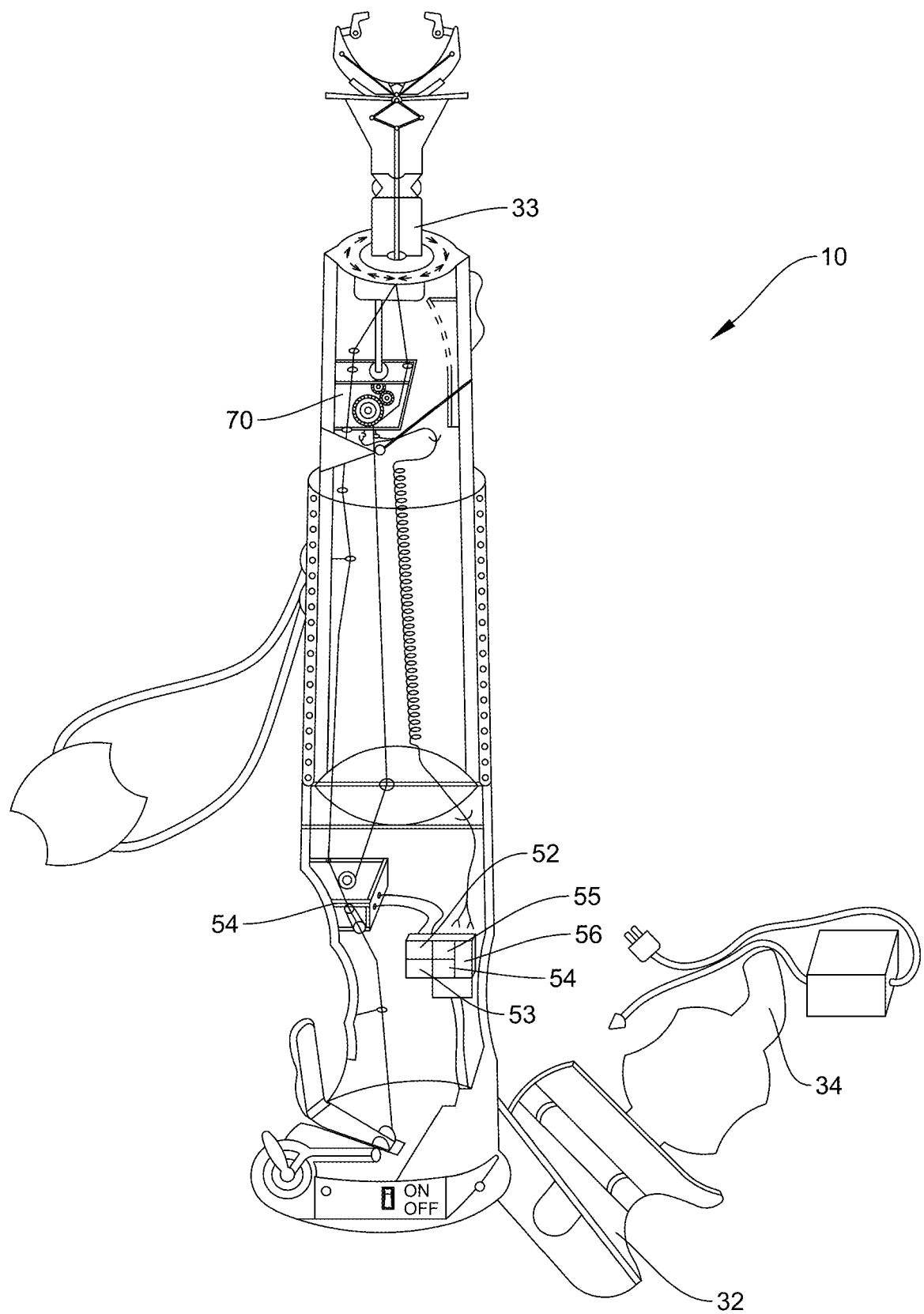
FIG. 3 is a partial cross sectional view thereof.
Figure 4:
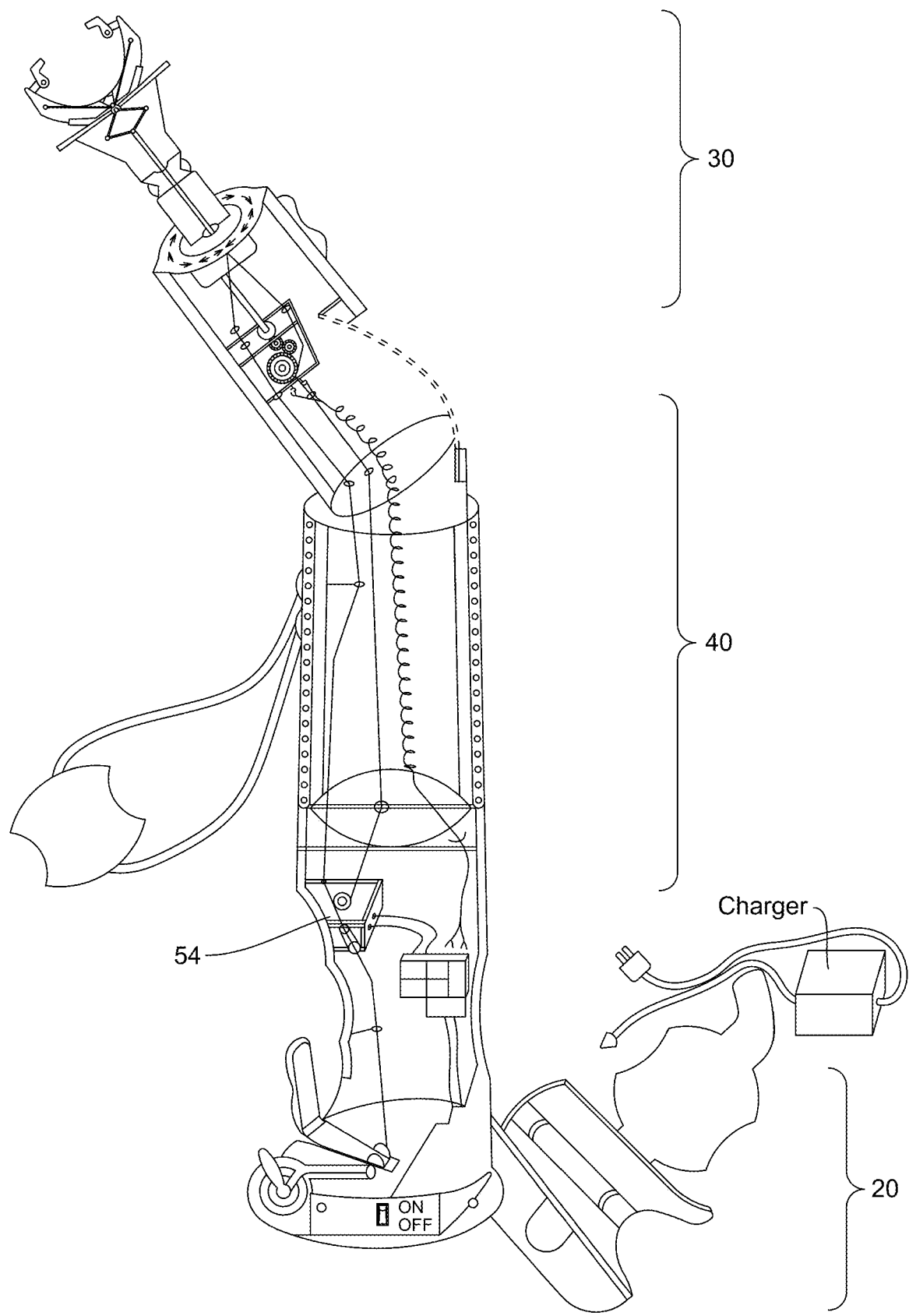
FIG. 4 is a partial cross sectional view thereof shown in an articulated orientation.

The best mode for carrying out the invention is presented in terms of its preferred embodiment, herein depicted within the FIGS. 2 through 4.

1. Detailed Description of the Figures

Referring to FIG. 2 through FIG. 4, a reaching and grabbing assist device ("device"), generally noted as 10, is shown according to an exemplary configuration to provide a reaching extension for aid in reaching out of distance objects. The device 10 includes a handle end 20 at a proximal terminus and a grasping end 30 at a distal terminus. An extendable cylinder 40 connects the handle end 20 to the grasping end 30.

The handle end 20 may include a cushioned wrist rest 32 with a hook and loop fastened closure 34 adapted for attachment to a user's hand, wrist or forearm. A control panel 50 may provide controls for the device 10, directing the grasping end 30 to articulate up (out) 52 or down (in) 53 or left 54 or right 55. A grip control 56 may allow actuation of the gripping claw 32, as described in greater detail below. A reversible servo motor 54 may be in operational communication between the control panel 50 and the functional elements of the device.

A wrist strap 60 may be connected to the device 10, and may be an extended length, up to 40 inches or more. A hand/shoulder support 62 may be connected to the strap 50.

The extendible cylinder 40 is supported at a proximal end by the handle end 20. The extendible cylinder 40 may include an outer base cylinder 42 that contains an extendable inner cylinder 44. The inner cylinder 44 may be manually rotated about an angular joint 45 such that rotation about the angular joint 45 will tilt the nested extendable inner cylinder 44 angularly about a lateral centerline. Such a rotation may be manually operated to position the distal portion to an incremental locking point. It is preferred that preset incremental locking points about the rotation may exist. It is more preferred that such present locations may be at 0°, 20°, 40°, 60°, 90° and 180° throughout its rotation.

A distal gearbox 70 may be provided, controlled by a reversible servo motor and operationally connected to the grasping end 30. The grasping end 30 may include an extendible shaft 33 to provide motorized linear extension. A connector 34 may provide a mechanical attachment for the gripping claw 32. The grip control 56 may be used to initiate the articulation of the gripping claw 32 in order to grasp about an object. Retention fingers 36 may be provided at the outer terminus of each claw 32 to aid in retaining of a grasped object.

2. Operation of the Preferred Embodiment

In operation, the device 10 may be used by anyone, and especially while shopping where merchandise may be stored on high shelving. By providing a motorized grasping extension, the device 10 may particularly useful to those disabled in wheel chairs, the little people community or those that are bedridden.

The foregoing descriptions of specific embodiments of the present invention are presented for purposes of illustration and description. The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way. Any unintended embracement of such subject matter is hereby disclaimed. They are not intended to be exhaustive nor to limit the invention to precise forms disclosed and, obviously, many modifications and variations are possible in light of the above teaching. The embodiments are chosen and described in order to best explain principles of the invention and its practical application, to thereby enable others skilled in the art to best utilize the invention and its various embodiments with various modifications as are suited to the particular use contemplated. It is intended that a scope of the invention be defined broadly by the Drawings and Specification appended hereto and to their equivalents. Therefore, the scope of the invention is in no way to be limited only by any adverse inference under the rulings of *Warner-Jenkinson Company, v. Hilton Davis Chemical*, 520 US 17 (1997) or *Festo Corp. v. Shoketsu Kinzoku Kogyo Kabushiki Co.*, 535 U.S. 722 (2002), or other similar caselaw or subsequent precedent should not be made if any future claims are added or amended subsequent to this Patent Application.

What is claimed is:

1. A reaching and grabbing assist device comprising:
    a handle end at a proximal terminus for holding and control by a user;
    an extendable cylinder extending from the handle end and further comprising:
        an outer cylinder element supporting a motor and a control interface;

at least one nested inner cylinder element nested within the outer cylinder element and extending or retracting therefrom by in a linear motorized manner by the motor, wherein said at least one nested inner cylinder element is further angularly articulated from a linear centerline; and a grasping end at a distal terminus operationally articulated by the motor via the control interface, wherein the grasping end further comprises a gripping clamp.

2. The reaching and grabbing assist device of claim 1, wherein said gripping clamp further comprises a gripping range of up to about 10 inches.

3. The reaching and grabbing assist device of claim 2, wherein said grasping end is further rotationally controllable.

4. The reaching and grabbing assist device of claim 1, wherein said grasping end is further rotationally controllable.

5. The reaching and grabbing assist device of claim 1, further comprising a hand and shoulder support strap affixed to and extending from the outer cylinder and extending at least 40 inches.

6. The reaching and grabbing assist device of claim 1, wherein said handle end further comprises:

a wrist rest in combination with a closure strap adapted for connection to a hand, wrist or forearm of the user.

7. The reaching and grabbing assist device of claim 1, wherein the grasping end is rotational position to an incremental locking point.

8. The reaching and grabbing assist device of claim 7, wherein said incremental locking point about a rotation is selected from a group consisting of: 0°; 20°; 40°; 60°; 90°; and 180°.

* * * * *